United States Patent
Sharp, II et al.

(10) Patent No.: US 11,515,026 B2
(45) Date of Patent: Nov. 29, 2022

(54) SYSTEM AND METHOD FOR DIGITALLY TRANSLATING NATURAL LANGUAGE PRESCRIPTION MEDICATION LABEL TO PROGRAMMATICALLY OPERABLE STRUCTURE FOR USE WITH SMART PILL CONTAINERS

(71) Applicant: Sharp Solutions LLC, Little Rock, AR (US)

(72) Inventors: Daniel S Sharp, II, Maumelle, AR (US); Zigmond Robert Gustafson, North Little Rock, AR (US)

(73) Assignee: Sharp Solutions LLC, Maumelle, AR (US)

(*) Notice: Subject to any disclaimer, the term of this patent is extended or adjusted under 35 U.S.C. 154(b) by 78 days.

(21) Appl. No.: 17/337,637

(22) Filed: Jun. 3, 2021

(65) Prior Publication Data
US 2021/0350894 A1 Nov. 11, 2021

Related U.S. Application Data

(63) Continuation-in-part of application No. 16/871,164, filed on May 11, 2020.

(51) Int. Cl.
| | |
|---|---|
| *G16H 20/13* | (2018.01) |
| *A61J 1/03* | (2006.01) |
| *A61J 7/00* | (2006.01) |
| *A61J 7/04* | (2006.01) |
| *G06Q 40/08* | (2012.01) |

(Continued)

(52) U.S. Cl.
CPC ........... *G16H 20/13* (2018.01); *A61J 1/03* (2013.01); *A61J 7/0084* (2013.01); *A61J 7/0418* (2015.05); *A61J 7/0481* (2013.01); *B65D 83/0454* (2013.01); *G05B 19/042* (2013.01); *G06F 40/40* (2020.01); *G06Q 40/08* (2013.01); *G16H 40/20* (2018.01); *G16H 40/67* (2018.01); *G05B 2219/25202* (2013.01)

(58) Field of Classification Search
CPC ........ G10L 15/18; A61J 7/0418; G16H 20/13; G16H 20/10; G07F 17/0092
USPC .................................................. 700/231–244
See application file for complete search history.

(56) References Cited

U.S. PATENT DOCUMENTS

| | | | | |
|---|---|---|---|---|
| 2006/0231109 A1* | 10/2006 | Howell | .................. | G16H 40/63 600/300 |
| 2017/0039342 A1* | 2/2017 | Nichols | .................. | G16H 70/40 |
| 2017/0293738 A1* | 10/2017 | Bender | .................. | G16H 10/60 |

* cited by examiner

*Primary Examiner* — Timothy R Waggoner

(57) ABSTRACT

A smart pill container and system integrating the same, combined with a method for digitally translating natural language prescription medication into a programmatically operable structure and form for use by the smart pill container system, where the digital translation includes the abstraction of a prescription frequency characteristic into a number of "slots" and the abstraction of a prescription temporary characteristic by creating an array of "as of" date and value pairs, allowing for the building of a patient's prescription schedule, where the smart pill container has a number of pill wells for storing different doses of medication, and where based on the prescription schedule, an opening in the pill container provides at least one user with access to the medication stored in a particular one of the pill wells at a given dosing time, and where a platform associated with the pill container provides instructions for dosing such medication and monitors use of the pill container for compliance with the prescribed medical regimen.

12 Claims, 13 Drawing Sheets

(51) Int. Cl.
*G16H 40/20* (2018.01)
*G05B 19/042* (2006.01)
*G06F 40/40* (2020.01)
*B65D 83/04* (2006.01)
*G16H 40/67* (2018.01)

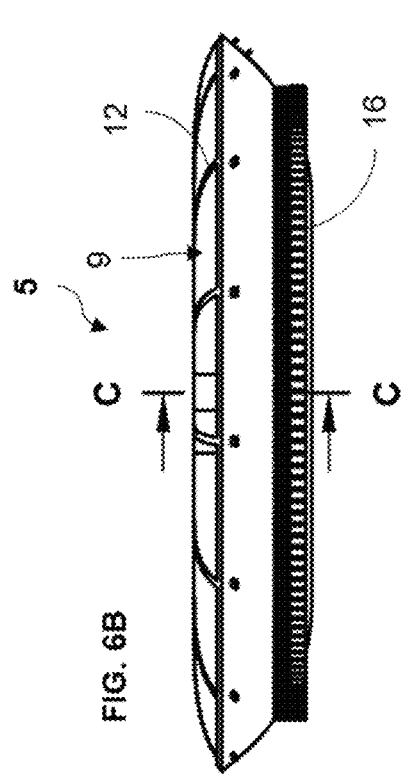
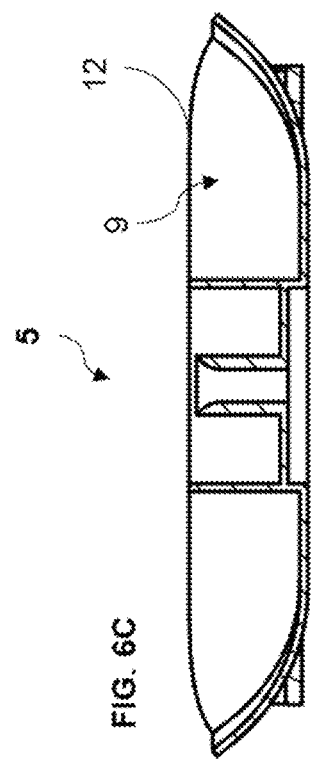
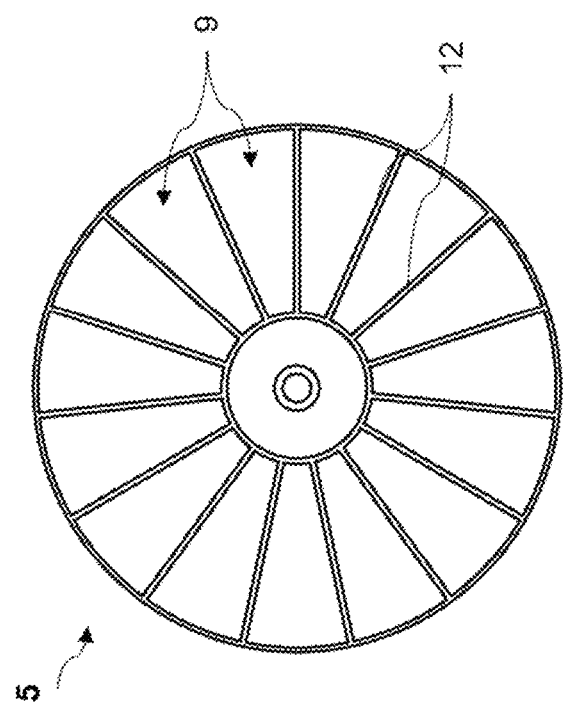

SYSTEM AND METHOD FOR DIGITALLY TRANSLATING NATURAL LANGUAGE PRESCRIPTION MEDICATION LABEL TO PROGRAMMATICALLY OPERABLE STRUCTURE FOR USE WITH SMART PILL CONTAINERS

CROSS REFERENCE TO RELATED APPLICATIONS

This application is a continuation-in-part application of U.S. patent application Ser. No. 16/871,164, filed on May 11, 2020, and entitled "Smart Pill Container Device and Platform System." Such application is incorporated by reference herein in its entirety.

STATEMENT REGARDING FEDERALLY SPONSORED RESEARCH OR DEVELOPMENT

Not applicable.

BACKGROUND OF THE INVENTION

According to data from the Centers for Disease Control and Prevention, nearly 50% of people in the United States used at least one prescription medication in the past 30 days, 24% used three or more prescription drugs in the past 30 days, and 12.6% used five or more prescription drugs in the past 30 days. In some cases, staying compliant with a daily regimen of prescribed medications can be the difference between having an otherwise uneventful day and taking a trip to the ER to begin a week-long hospital stay. In some cases, compliance with a stringent medication regimen falls solely on the patient. In other cases, however, the patient may not have full dependence or may not fully understand the importance of strict compliance with the daily regimen. In these cases, ensuring compliance may be the responsibility of a parent, spouse, friend, or other loved one, or in some cases may even be the responsibility of a professional nurse or caretaker. Wherever the responsibility may fall, strict compliance with the daily regimen is a necessary, and often difficult, task.

For example, for one patient, who suffered a traumatic head injury as a child resulting in sever seizures and some cognitive impairment, a daily regimen of six medications totaling over twenty pills per day (which must be taken at multiple times throughout the day) is required to control seizures and prevent unwanted trips to an emergency department or hospital. With this strict regimen there is little margin for error. Caretakers, who often are juggling multiple responsibilities, do their best to make sure that the right medication is taken at the right time. But even despite the best efforts of caretakers, sometimes there is a failure in compliance with the regimen. Common failures may arise where a patient (or their caregiver) gets confused on which day of the week it is, which may end up causing the patient to mistakenly take a medication twice in the same day. Other times, a patient or caregiver may not administer the medication at all—whether because the patient is not feeling up to taking medication, or simply forgets, or whether there has been some other mistake.

These issues aren't new issues and many products have been developed to assist patients and their caregivers in administering medications in compliance with a strict daily regimen. The most commonly used product for maintaining compliance with a medicine regimen is a simple pill container with individual compartments for each day of the week, typically with the day of the week for each compartment labeled accordingly so that the patient knows which medicine to take on a particular day. These simple products, however, are only as reliable as the person or persons who are responsible for the continued refilling of these products and are not helpful in the situation where the patient may not recall which day of the week it is. These simple products also do not provide alerts or notifications if a day is missed (or if multiple days' medication is taken on a single day) and do not help patients or their caregivers keep track of refill deadlines or other similar information. Plus, without certain smart controls, these existing containers do not help in preventing the patient from taking too many doses or the wrong dose.

In order to overcome these problems and to save the lives of many, the inventors hereof have recognized a need for a system and device with smart capabilities that not only allows for the organization of multiple medications into time-dedicated groupings (such as, for example, daily grouping of medications for an entire week) but also includes safeguards that prevent the administration of medicine on a day where medicine has already been taken, that alert the patient or caregiver that a dose has been missed, and that assists the patient and caregiver in the loading of medication into appropriate groupings and in the calculation and reminder of when it is time to request refills. It is an aim of the inventors hereof to drastically improve the independence of patients so that compliance with a prescribed regimen can be achieved without dependence on caregivers or loved ones.

In order to facilitate this independence, the inventors hereof have recognized the inherent limitations of digitally capturing prescription medication information for use in such a smart pill container. Pill bottle labeling includes natural language information for characteristics associated with the prescription, including information like the medication name, the dosing frequency in lay terms (e.g. one tab, twice daily), the strength of the medication (e.g. 100 mg), the quantity of medication in the prescription when full (e.g. 60 tablets), how many refills are remaining, and the refill expiration date. The inventors hereof have recognized that, while this prescription medication information can be captured for use in such a smart pill container using traditional data storing means (namely, by storing each piece of natural language data into a column or field corresponding to the fields on the prescription label), such data storing means introduces an undo complexity into the smart pill container system, particularly when the user is asked to specify the times of day to satisfy the dosing frequency prescribed. Thus, the inventors hereof have recognized that with a novel system and method for digitally translating the natural language information from the prescription label into a structure and form that can be operated on programmatically, the technological efficiency of the smart pill container, and others like it, can be maximized. Furthermore, to maximize efficiency of the technology and increase user experience even more, it is recognized that centralized control of the logic associated with the integrated pill container system is desirable.

BRIEF SUMMARY OF THE INVENTION

The present invention is directed to a system and method for digitally translating prescription label information provided in natural language form on the prescription label to a programmatically operable structure allowing the prescription label information to be input into and manipulated by a software platform integrated with a smart pill container. The smart pill container and integrated software platform not only provides a regimen-keeping pill container, but also provides a user interface and platform that allows for the smart integration of the pill container with user devices that can track compliance with the medicine regimen and send alerts based on compliance or non-compliance with the regimen (including alerts indicating the need to request refills for prescribed medications). The digital translation of the natural language prescription information into the programmatically operable structure and form increases the technological efficiency of the smart pill container and integrated platform.

In this regard, it is an object of the present invention to increase a patient's medication adherence, which is accomplished by integrating a specially-manufactured pill container with user devices (such as smartphones or computers), web technologies, and backend server components, allowing for the patient, caregivers, and health care industry providers (such as insurance providers, pharmacies, and health care providers) to communicate effectively regarding the patient's adherence to their prescription regimen and by introducing prescription label information into the system in a structure and form that is programmatically operable by the system in order to provide a device and system that is easier to manage and improves the user experience. Further, the centralization of all data associated with the pill container at a centralized server allows for the more efficient monitoring and operating of the pill container system.

These and other objects, features, and advantages of the present invention will become better understood from a consideration of the following detailed description of the preferred embodiments and appended claims in conjunction with the drawings as described following:

BRIEF DESCRIPTION OF THE DRAWINGS

FIG. 6A is a top view of one embodiment of the pill carriage of the pill container of the present invention.

FIG. 6B is a side view of one embodiment of the pill carriage of the pill container of the present invention.

FIG. 6C is a cut-away side view of one embodiment of the pill carriage of the pill container of the present invention, taken from view C-C of FIG. 6B.

DETAILED DESCRIPTION OF THE INVENTION

Figure 1:
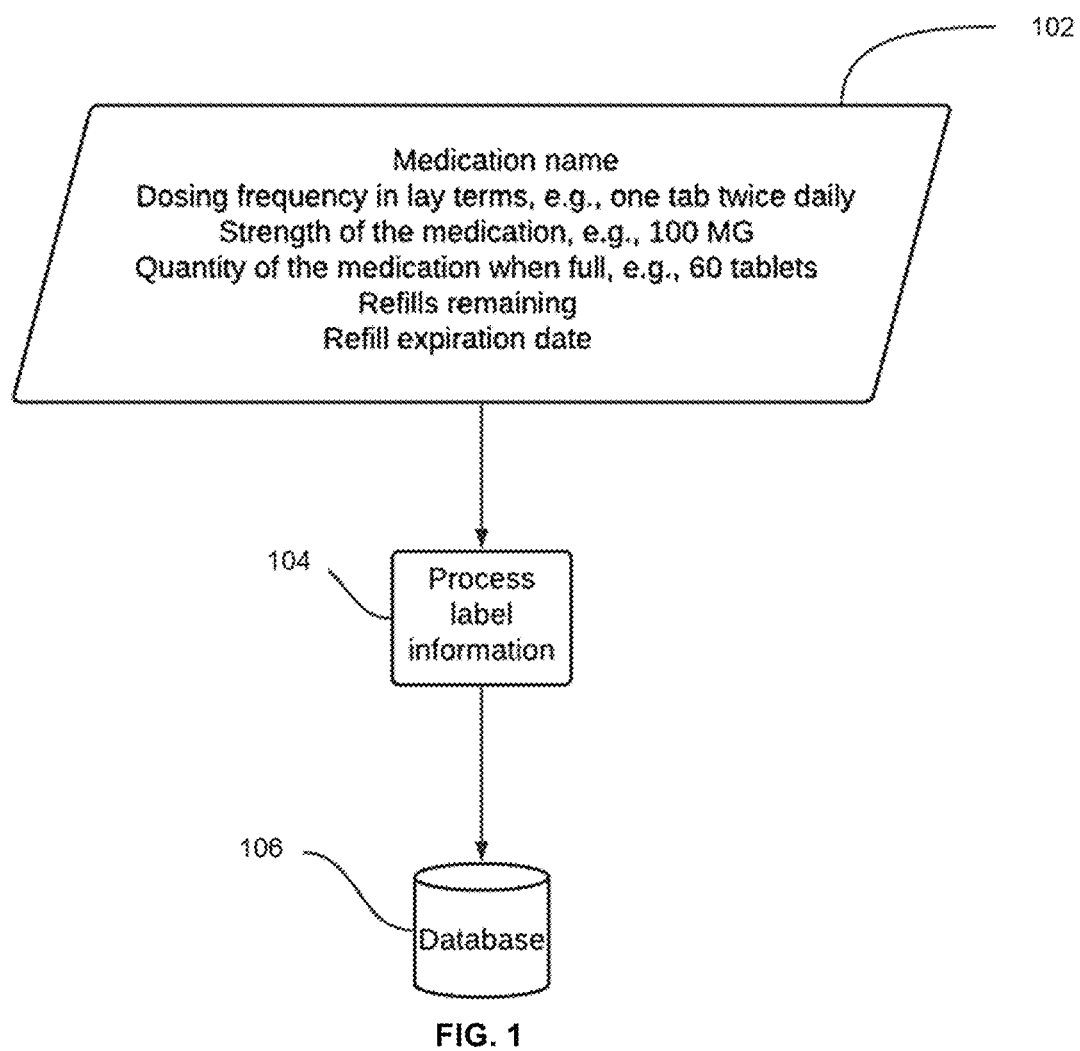
FIG. 1 is a process flow diagram showing one embodiment of the method for digitally translating prescription label information.
Figure 2:
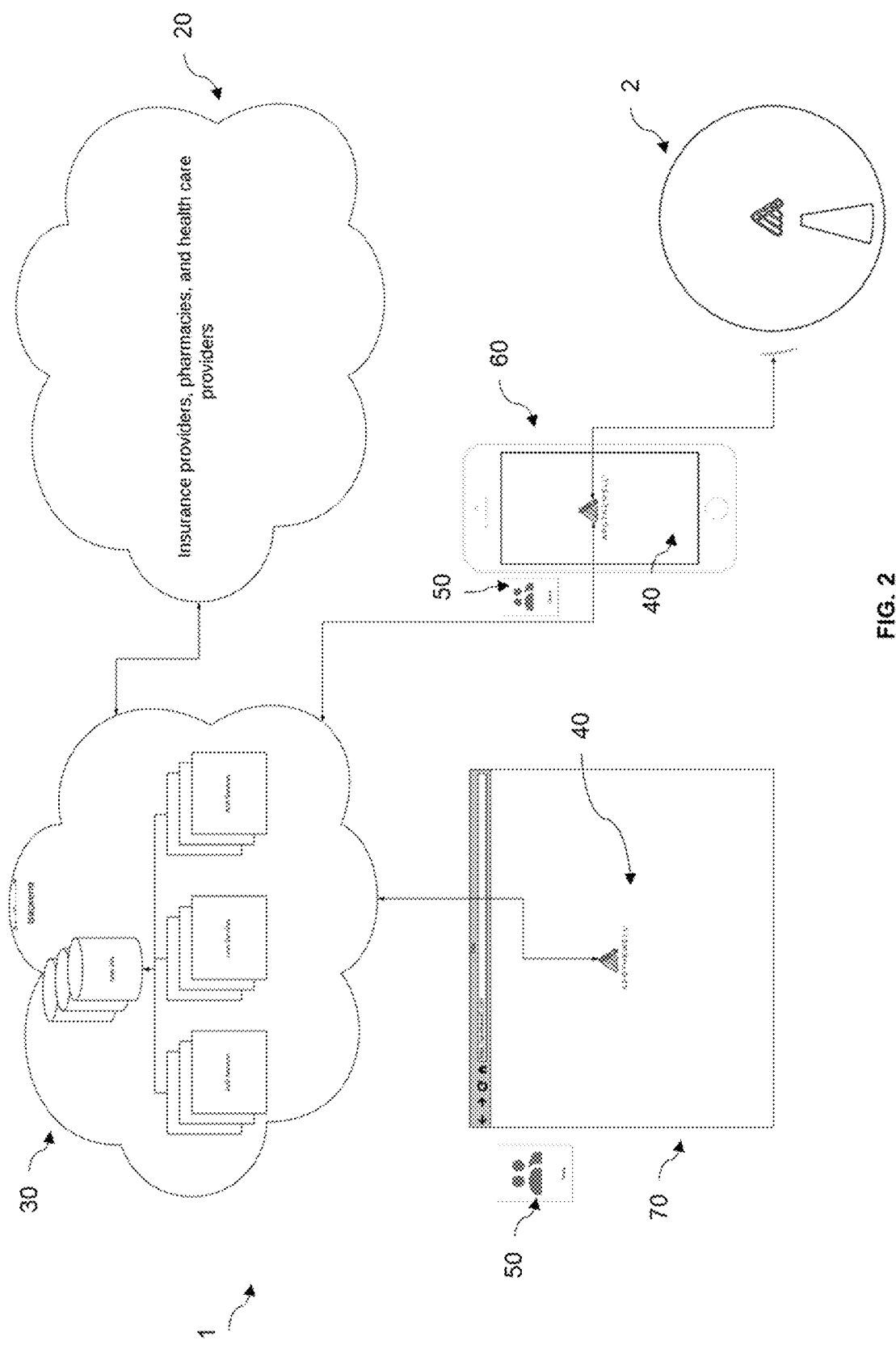
FIG. 2 is schematic diagram showing the connectivity of pill container, platform, backend services, and users of the system of the present invention
Figure 3:
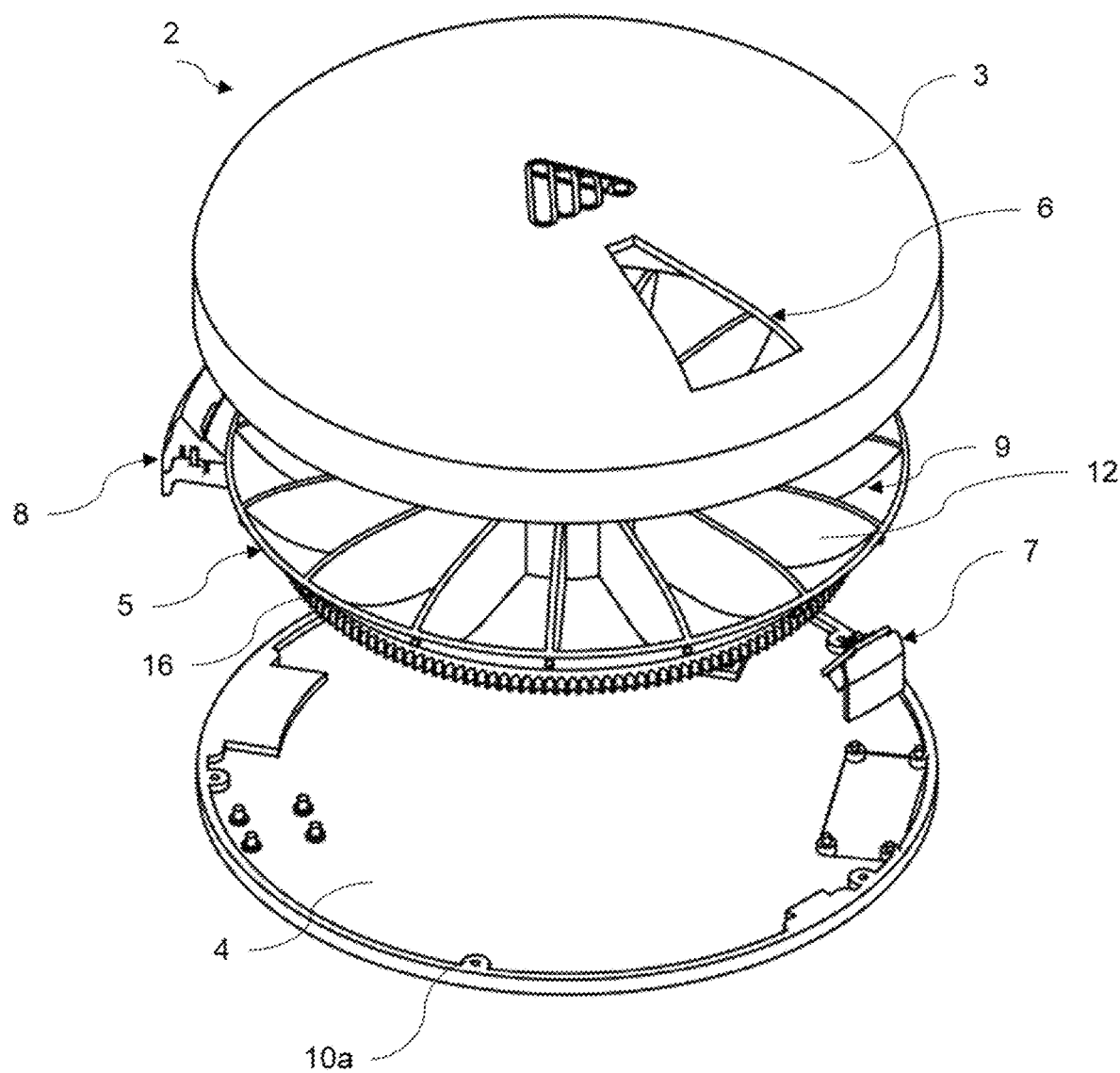
FIG. 3 is an exploded top-view of one embodiment of the pill container of the present invention.
Figure 4:
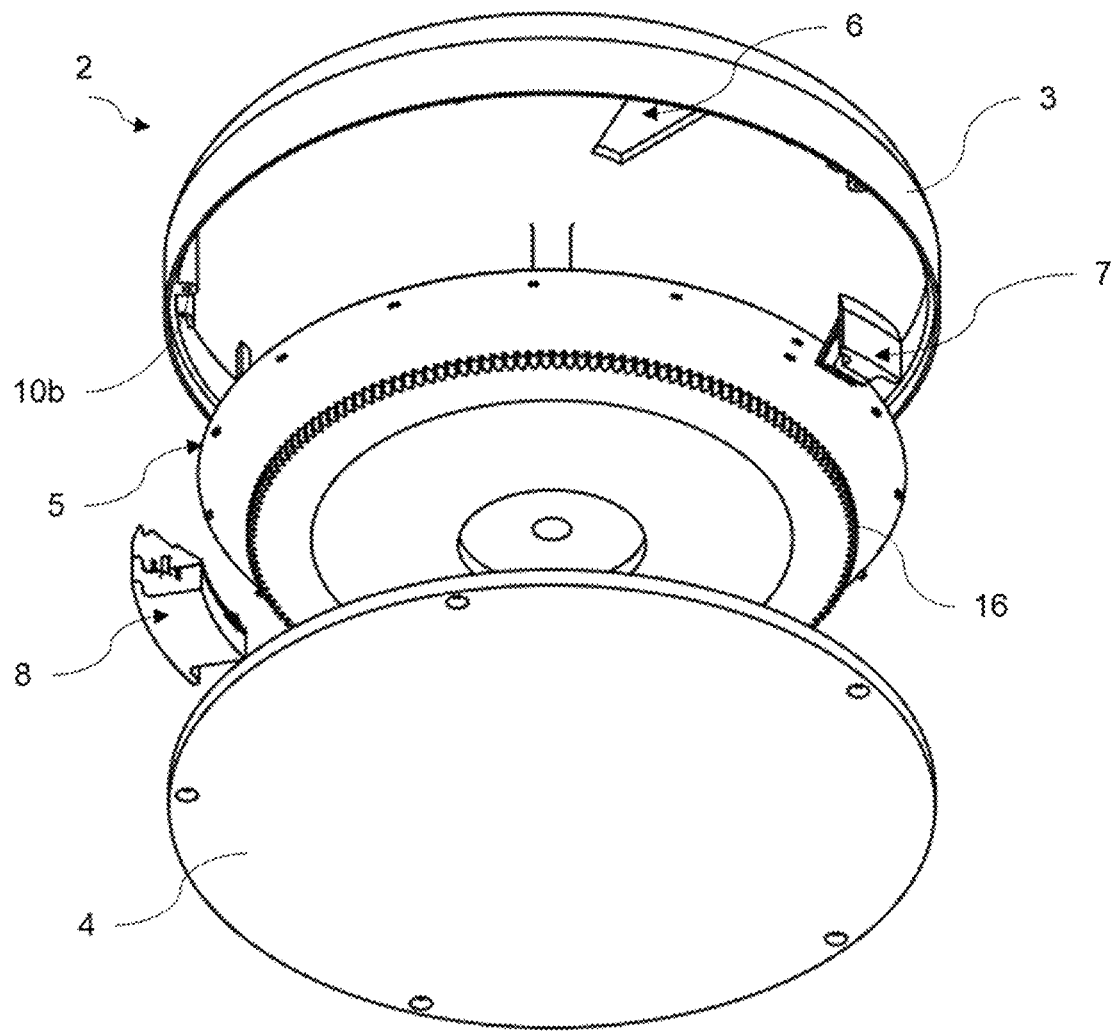
FIG. 4 is an exploded bottom-view of one embodiment of the pill container of the present invention.
Figure 5:
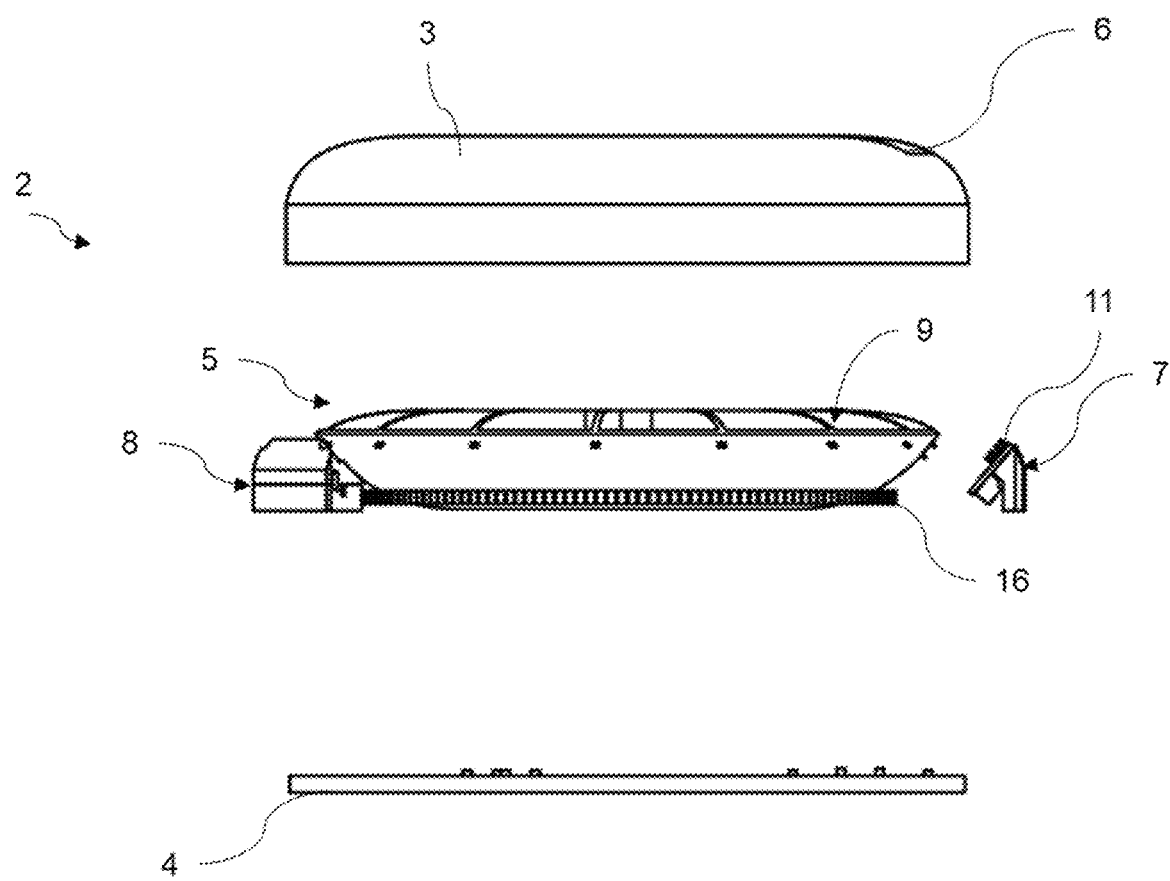
FIG. 5 is an exploded side-view of one embodiment of the pill container of the present invention.
Figure 7D:
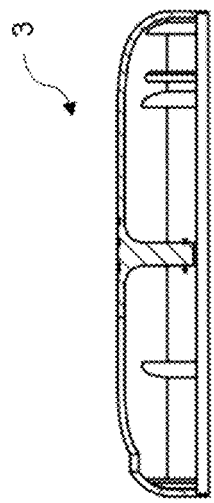
FIG. 7D is a cut-away side view of one embodiment of the top plate of the pill container of the present invention, taken from view D-D of FIG. 7C.
Figure 7E:
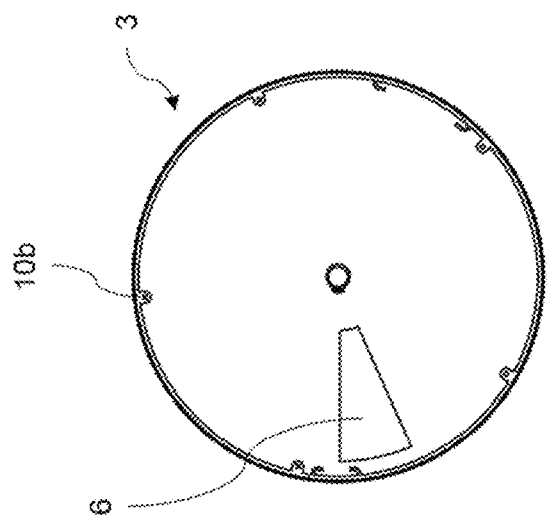
FIG. 7E is a bottom view of one embodiment of the top plate of the pill container of the present invention.
Figure 7A:
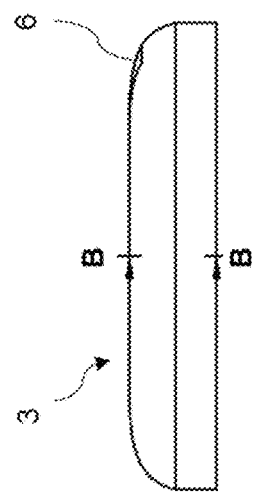
FIG. 7A is a side view of one embodiment of the top plate of the pill container of the present invention.
Figure 7B:
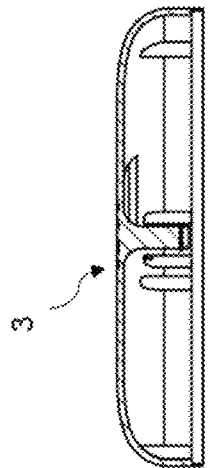
FIG. 7B is a cut-away side view of one embodiment of the top plate of the pill container of the present invention, taken from view B-B of FIG. 7A.
Figure 7C:
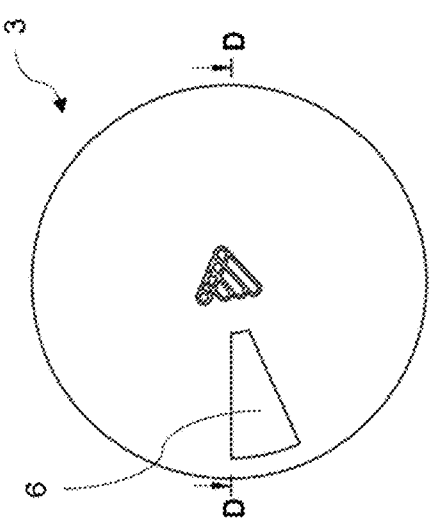
FIG. 7C is a top view of one embodiment of the top plate of the pill container of the present invention.
Figure 8A:
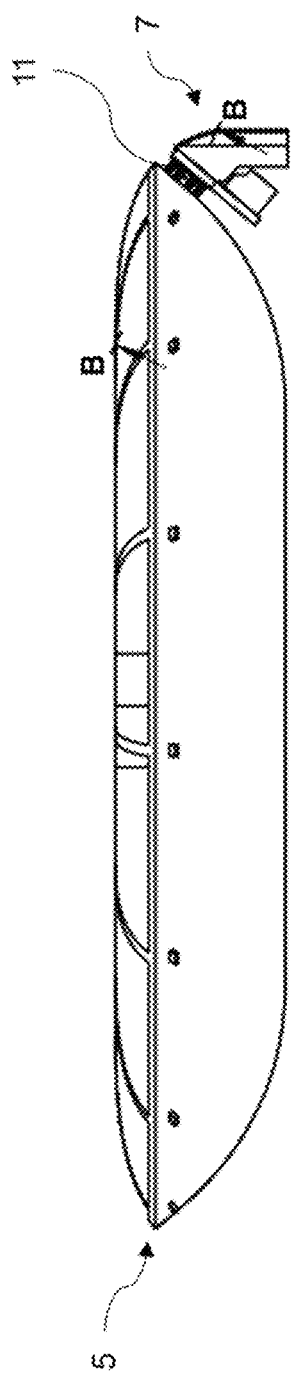
FIG. 8A is a side view of one embodiment of the pill carriage of the present invention, showing one embodiment of the positioning system of the present invention.
Figure 8C:
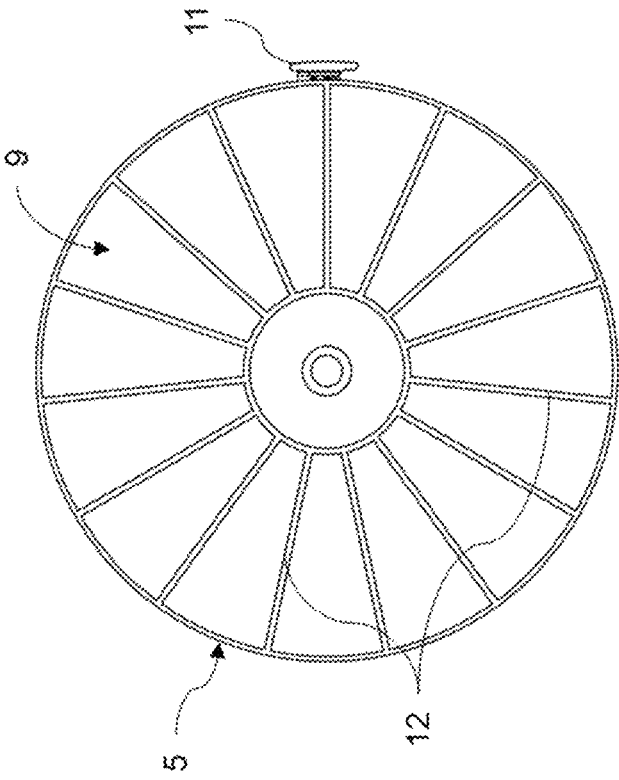
FIG. 8C is a top view of one embodiment of the pill carriage of the present invention, showing one embodiment of the positioning system of the present invention.
Figure 8B:
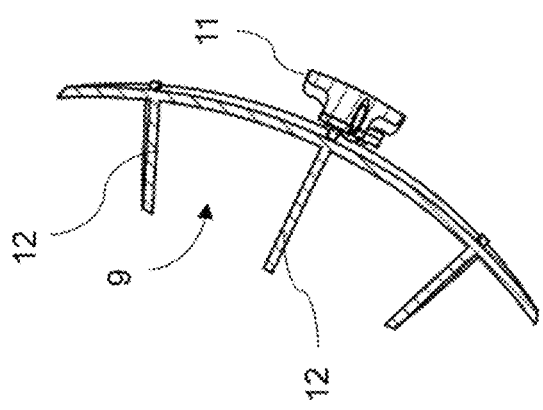
FIG. 8B is a cut-away view of the positioning system of the pill carriage of the present invention, taken from view B-B of FIG. 8A.
Figure 9B:
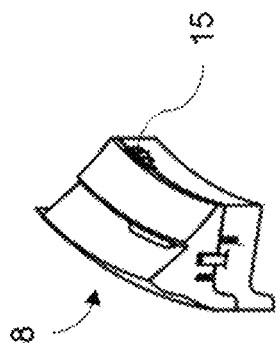
FIG. 9B is a view of one embodiment of the drive system of the present invention.
Figure 9C:
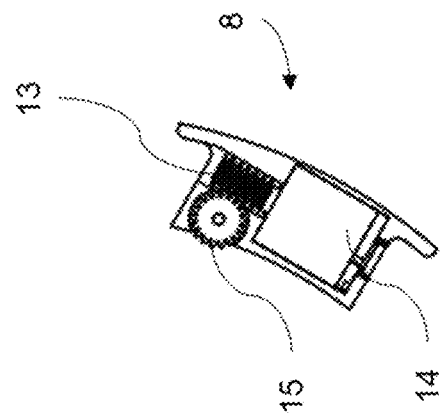
FIG. 9C is a view of one embodiment of the drive system of the present invention.
Figure 9A:
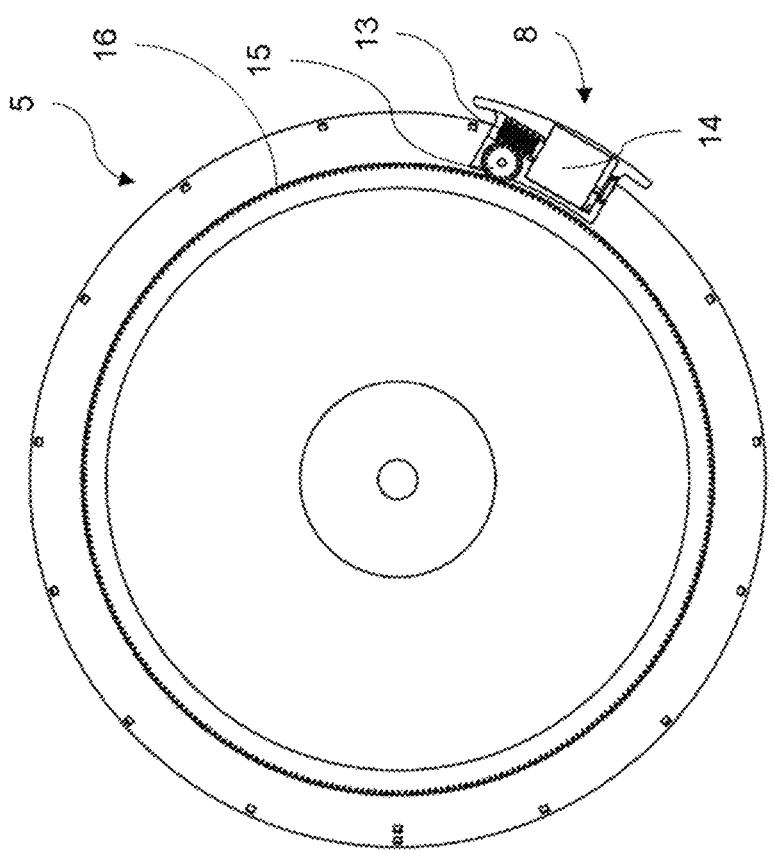
FIG. 9A is a bottom view of one embodiment of the pill carriage of the present invention, showing one embodiment of the drive system of the present invention.
Figure 10:
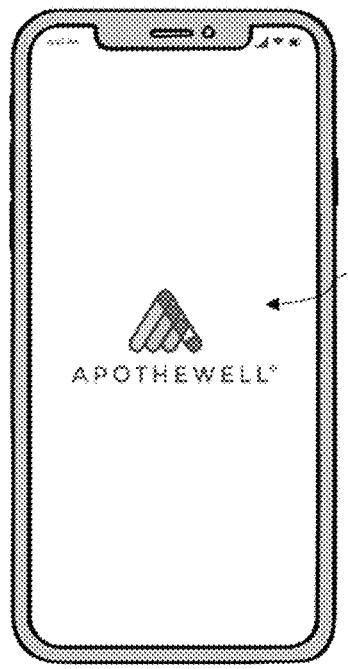
FIG. 10 shows one embodiment of the home screen interface of the platform of the present invention.

Generally speaking, the present invention is directed to a smart pill container 2 and a system 1 integrating the smart pill container 2 with a monitoring platform 40 accessible by one or more users 50 at user devices 60 (which may each be associated with, for example, the patient, a caregiver, multiple different caregivers, health care providers, etc.) and a system and method for digitally translating natural language prescription language information into a structure and form that is programmatically operable to be used by the smart spill container 2 and system 1 to increase the technological efficiency of the smart spill container 2 and system 1 and to increase the user experience for the same.

The smart pill container 2 is generally operable to organize and store various medication according to a prescribed regimen provided by a health care provider 20 (such as a doctor or pharmacy) and the integrated functionality of the smart pill container 2 with a platform operable at user devices 60 allows for the tracking and monitoring of compliance with the prescribed regimen from one or more user devices 60, while the digital translation of the prescription language information from its natural language form to a more programmatically operable structure and form allowing the system to more efficiently facilitate compliance with the prescribed regimen.

Before speaking specifically about the preferred embodiments of the smart pill container 2 and platform system 1, it is important to note that the pill container 2 and platform system 1 exist to increase the independence of a user following a prescribed medical regimen. In this regard, the smart pill container 2 is communicatively connected across a network to a platform 40 providing access to operation of the smart pill container 2 and data related to the smart pill container 2. The smart spill container 2 is a specially manufactured device that stores a patient's medication, provides and limits access to the medication based on a set medical regimen, and records and monitors usage data associated with the medication stored in the smart pill container 2, which can be accessible by users 50 affiliated with the smart pill container 2. For purposes of describing the invention, the term "patient" refers to a person who has been prescribed a medical regimen, while the term "user" refers to a person who operates the smart pill container 2 and connected platform 40. It may be seen, then, that in various embodiments the patient is the sole user, the patient is one of many users, or the patient is not a user at all. For example, in one embodiment, the system 1 may be suitable for use by a single adult user who merely needs better organization for tracking their own compliance with a prescribed medical regimen. In this case, the single user 50 is also the patient (where the patient is also a user, the term "patient-user" may be utilized to denote that the patient is both a patient and user), as the medical regimen associated with the pill container 2 has been prescribed to that patient-user, and it is that patient-user who is charged with taking the medicine contained in the pill container 2. In a second embodiment, it may be seen that there are many users 50 associated with a particular smart pill container 2, and only one of those users 50 is the patient. For example, where the patient is a minor or partially dependent on one or more parents or caregivers but still has the ability to maintain some personal independence, it is contemplated that the patient has independent access to the smart pill container 2 in order to maintain his or her own compliance with the prescribed medical regimen, but parents or guardians may also have access to the smart pill container 2 and connected platform 40 functionalities in order to monitor the patient-user's compliance. In this embodiment, there is a patient who is a patient-user and there are other users 50 (parents, caregivers, etc.) who are non-patient users. All of the users 50 (the patient-user and non-patient users) may receive the alerts and other monitoring functionality associated with the pill container 2 even if only the patient-user is taking the prescribed medication, and even if the patient-user is primarily in charge of loading the pill container 2 and self-administering the medication therefrom. In yet another embodiment, it may be seen that the patient may not be a user 50 at all. Instead, all users 50 are caregivers or other non-patient users 50. This may be seen particularly in situations where the patient has little to no independence and is dependent on one or more caregivers for maintaining the prescribed medical regimen. This may be, for example, where the patient is a very young child and a parent is required for administering the prescribed medication. Alternatively, for example, this situation may arise where the patient is an elderly patient in an assisted living facility, is an adult with impaired cognitive abilities, or is somehow otherwise entirely dependent on another person for maintaining compliance with a prescribed medical regimen. In this case, it may be seen that the pill container 2 still holds the patient's medications, but it is a non-patient user who accesses the medication(s) stored in the pill container 2 and receives the alerts or otherwise monitors compliance with the prescribed medical plan using the platform 40 of the present invention. The pill container 2 and system 1, although not used personally by the patient, still allows the caregivers or other non-patient users 50 to help track their responsibilities with regard to maintaining the patient's compliance with his or her medical regimen.

No matter the situation in which a smart pill container (whether that described with regard to the preferred embodiments below or any other smart pill container) is being used, it may be seen that it is necessary to create a system that can translate the natural language information from prescription labels into user guidance on when to take prescribed medication and guidance on loading the pill container for use by the patient. In order to do so, the natural language information on the prescription label must be transformed from its existing natural language from into a structure that can be easily operated on programmatically, resulting in increased efficiency of the smart pill container and platform and improve overall user experience of the smart pill container.

Prescription medication labeling often includes several types of information related to the prescription, including, for example (a) the medication name, (b) the dosing frequency (often in lay terms like "one tab twice daily"), (c) the strength of the medication (e.g. 100 mg), (d) the quantity of the medication when the prescription is full (e.g. 60 tablets per bottle), (e) the number of refills allowed and/or remaining, and (f) the refill expiration date. There may also be other similar information relating to the prescription. All of this information is placed on the prescription label in natural language. One way to capture that information for use in a smart pill container system would be to store each piece of data into a column or field corresponding to the fields on the label, and then prompt the user to specify the times of day to satisfy the frequency prescribed and store that with the corresponding fields. This approach can work but introduces an undo complexity into the surrounding systems. Take as an example, the user picks a scheduling time of 6 am and 6 pm to satisfy the twice-daily regimen, and then the prescription is later changed to three times daily. In natural language, we understand that three times daily most often means morning, noon, and evening. To accommodate that in this type of storage system, the surrounding system must introduce logic to recognize that moving from twice daily to three times daily is actually inserting a time slot between the morning and evening, not appending a time slot after the evening. Further, the surrounding system for that model most also process all data with every change of any data to recreate the overall schedule and load guidance.

Another complexity that is not addressed in the above structure is the timing of changes. Any person who is taking daily medications for extended periods of time, will have that medication change over time. They will be adding new prescriptions, removing old, and modifying existing. Using the most obvious storage example mentioned above, the resolution of these issues is pushed again to the surrounding systems. The eventual result is an overall system that is hard to manage and prone to issues that lead to a poor user experience. A much-improved system can be derived by abstracting the frequency and temporal aspects, creating a storage mechanism for each of these aspects, and managing them separately, only combining the two when needed to create a daily schedule or load guidance for a specific point in time.

To explain this process more clearly, the abstracting of medication frequency can be discussed first. The storage mechanism for frequency must recognize that medication take over extend periods of time is prescribed using common times of day, even if that time of day is not specifically mentioned, i.e., morning, noon, evening, and bed-time. Of course, not everyone's morning happens at the same time or even, for some, actually in the morning hours. Instead, the implied meaning is the time after waking. Abstracting this, frequency can be characterized as a first period, or slot, of time that happens after waking and then three more slots that happen approximately six hours apart from each other. Assume that the act of waking is zero hour then slot one would around the zero-hour mark, slot two around the six-hour mark, slot three around the twelve-hour mark, and the slot four around the eighteen-hour mark. But not everyone will take their medication exactly when waking up and at six hour increments thereafter. So, the true abstraction requires the creation of four slots of times and allow a user to specify their own time for each slot as a completely separate event. This way, any subsequent changes to the slot times can be managed and controlled independently of the medication assigned to corresponding slots. And while the use of four slots makes the most sense, there is nothing in this abstraction that prevents using more slots. The abstraction could have eighteen slots, one for each waking hour, or any other number of slots, depending on need and design.

The next abstraction is to set the frequency to specific slots. Medication taken multiple times a day needs to be distributed equally throughout the day, therefore twice a day requires the use of slots one and three OR two and four to meet the requirement. No other combination is allowed. In the extreme example of eighteen slots a day, medication taken five times a day should be allocated to slots one, five, nine, thirteen, and seventeen OR slots two, six, ten, fourteen, and eighteen. Those are the only two combinations that result in evenly spaced medication. Using the simpler, and more common, four slots per day, the combinations are easy to handle as shown in the following possible scenarios: (a) medication taken once daily can be assigned to any of the four slots, (b) medication taken twice daily can only be assigned to slots one and three OR two and four, (c) medication taken three times daily can only be assigned to slots one, two, and three OR two, three, and four, and (d) medication taken four times daily is assigned to all four slots. As shown, the possible combinations are restricted based on the frequency of the prescribed medication by ensuring that the medication is taken at equal intervals. In this regard, a medication taken three times per day would not work with a combination of slots one, three, and four, because there would be a longer period between the first and second doses (slots one and three) than the second and third doses (slots three and four), which would not be effective for the prescription. When the frequency of a given medication changes, managing the process is as simple as presenting the user with the appropriate set of options and letting them choose the option best for them. For example, take the scenario of moving from twice a day to three times a day. If the user is currently using slots one and three, the user can choose to add slot two OR remove slot one and add slots two and four. This is a scenario that can be coded and presented to the user easily. Further, not all medication is taken daily. Some medication is taken one or more times weekly or one or more times monthly. This same abstraction can be moved now to cover the days of the week or month. In the weekly example slots now represent a day of the week, i.e. Sunday thru Saturday, and in the monthly example slots represent calendar days. The same rules of equal distribution apply and medication taken weekly or monthly can be allowed to use any daily slot.

Having described the abstraction of the frequency abstract into a programmatically operable form, the abstraction of the temporary aspect of medication management can be discussed. All aspects of a medication can and will change over time. Simply replacing the data as it changes removes, or significantly complicates, the ability to schedule future changes and recognize changes in the past. Instead, each field needs to be stored with an "as of" date to create an array of date and value pairs. This way finding a value for a given date becomes a process of finding the closest date in the array that is still less than, or equal to, the given date and returning the value associated with that date. Combining these two abstractions, the user's daily schedule can be built by getting the "as of" values for each field for the given date, mapping the frequency value to the slot abstraction, and then applying the specific times of day the user has given for each slot. Similarly, guidance can be built to step a user through loading their pill case by creating the schedule for several consecutive days and then extracting the medication name, dosage and time of day. This information can then be turned into simple instructions, e.g. "place two tables of the medication labeled XYZ into the pill case slot for Monday morning, 8 am medications". Running through each of the medications will result in the proper guidance.

Turning to FIGS. 2-8C one embodiment of the pill container 2 of the present invention may now be described. The pill container 2 may generally be described as a container for storing and administering medications according to a prescribed medical regimen. The pill container 2 is formed from a housing that has a top portion 3 and a bottom portion 4 that fit together to form an internal compartment, where various components of the pill container 2 are housed. First, a number of spaced-apart walls 12 are positioned inside at least a portion of the internal compartment to create a number of individual storage slots 9 inside the container 2. These storage slots 9, which may be referred to herein as "pill wells," are where the medicine to be administered to the patient is stored. The medicine may be stored in the pill wells 9 according to a prescribed medical regimen in one of a variety of ways, as discussed more fully below. Any number of pill wells 9 can be provided as desired, but, of course, the less pill wells 9 that are included the more often the user must restock the medication into the pill container 2. It would be preferred, then, that the pill container 2 at least include a sufficient number of pill wells 9 to last about a full week worth of medication (preferably with seven, fourteen, or twenty-one slots 9, for example, which would allow for use with medical regimens requiring only one dose per day, two doses per day, or three doses per day for an entire week). For example, the container 2 may be configured such that there are seven pill wells 9. It may be seen, then, that each pill well 9 corresponds to a different day of the week, with each pill well 9 containing the medicine for a specific day of the week. This configuration, of course, is better suited where only a single dose is required each day. Alternatively, the container 2 can be configured such that there are fourteen pill wells 9. This particular configuration may be particularly useful in cases where a prescribed medical regimen requires two doses per day, because each of the pill wells 9 can contain a single dosage (thus, two pill wells 9 for each day of the week) so that a full week worth of medicine can be stored in the container 2 but the medicine can still be split into separate doses. Alternatively, in cases where the prescribed medical regimen requires three separate doses of medication per day, the container 2 can be configured with, for example, twenty-one pill wells 9, allowing for a full week worth of doses. Of course, other configurations are possible as well, for example, in the case where three separate doses per day is required, a container 2 including nine pill wells 9 would allow for three days' worth of separate dosages to be stored in the container 2 (three pill wells 9 per day, each pill well 9 storing a different dose). While this would require restocking of the medication in the pill container 2 more often, it would still provide many of the great benefits of the smart pill container 2 and system 1. It is preferred, of course, that the number of pill wells 9 correspond to a certain number of doses, meaning each pill well 9 preferably corresponds only to a single dose, not multiple doses per pill well 9, which will allow for the easier separation of individual doses so that mis-doses do not occur. Regardless of the number of pill wells 9, once all of the medication for all pill wells 9 is administered (which may be referred to as a full rotation), the pill wells 9 can be restocked with the appropriate medications per dose. In one embodiment, however, a full rotation is not required before replenishing the pill wells 9 takes place, and load guidance 49 by the platform 40 allows for restocks to happen at any point when even a single pill well 9 is empty.

As noted above, the pill container 2 is generally formed from a housing having a bottom plate 4 and a top plate 3 that fit together to form the general housing and internal compartment. In one embodiment, the bottom plate 4 and top plate 3 can fit together using mounting pieces 10a, 10b, such that the pill container 2 stays substantially together unless sufficient force is applied to separate the top plate 3 and bottom plate 4. In the preferred embodiment, the housing has an opening 6 positioned such that the user can access the medication stored inside the pill container 2 even when the housing is fit together (i.e. providing the user access to the internal storage compartment). In the preferred embodiment, only one internal pill well 9 is accessible at a given time, thereby allowing a user to remove the medication only in that pill well 9 at the appropriate time (according to a prescribed medical regimen) while keeping all other pill wells 9 closed or in accessible (to avoid mis-dosing). In the preferred embodiment, the opening 6 is positioned in the top plate 3 of the housing. Because the opening 6 only provides access to a single pill 9 well at a time, it is understood that in order to access medication in a second pill well 9, either the opening 6 or the pill well 9 must move such that the opening 6 aligns with the new pill well 9.

In the preferred embodiment, the opening 6 is stationary (meaning that the housing does not move), and thus, in order for different pill wells 9 to be accessed at different times, the internal pill wells 9 must be movable such that each pill well 9 can be moved to a position corresponding to the stationary opening 6 at different times. It may be seen, then, that in the preferred embodiment the pill wells 9 are positioned on a rotating element 5 such that rotation by the user allows for a different pill well 9 to be exposed by the opening 6 at different times (this rotating element 5 may be referred to herein as a "pill carriage" 5 because it stores and moves the pills according to the movement described herein). The pill carriage 5 is rotatable within the pill container 2 as to allow for movement of a new pill well 9 to the position corresponding to the opening 6, therefore allowing access to the medication in that pill well 9 at that time. The rotational movement of the pill carriage 5 is described more fully below.

In one embodiment, the opening 6 is covered by a lid such that the opening 6 can be placed in a closed position when no administration of medication is taking place as to act as a lid on the otherwise exposed pill well 9 that is in the position corresponding to the opening 6 at a given time. The lid (which may, for example, be hinged to the housing) can be opened to give access to the medication in the pill well 9 when appropriate. In one embodiment, the pill carriage 5 and bottom plate 4 of the housing are mechanically (but rotatably) fastened to one another so that they remain attached during use of the pill container 2, such that the top plate 3 of the housing can be removed such that the pill wells 9 are all exposed simultaneously (as opposed to when the top plate 3 of the housing is attached to the bottom plate 4 and only one pill well 9 is exposed by the opening 6 in the top plate 3) such that the pill wells 9 can be restocked with medications, cleaned, or otherwise accessed simultaneously as necessary. In an alternatively embodiment, it is contemplated that the pill carriage 5 does not rotate, but, instead, the top plate 3 is rotatable such that the opening 6 in the top plate 3 can be rotated to different pill wells 9 as desired. However, because it may be easier to house certain mechanical components positioned inside the pill container 2 (as discussed below) to facilitate the rotation and locking of the pill carriage 5, it is preferred that the pill carriage 5 is rotatable and the top plate 3 is stationary.

While it is contemplated that the rotation of the pill carriage 5 can be a manual rotation (i.e. by the user manually and physically rotating the pill carriage 5), in the preferred embodiment the rotation of the pill carriage 5 can be selectively caused through an electronically automated system (i.e. the use of motorized components to rotate the pill carriage 5). For example, in the preferred embodiment, a motorized drive system 8 is used. The drive system 8 is preferably housed in the pill container 2 as to hide the motorized components from outside elements. The drive system 8 is configured such that the pill carriage 5 includes a number of gear cogs 16 around its outer edge (preferably the bottom outer edge), as shown. A rotating gear 15 is mounted inside the container, preferably on or near the bottom plate 4, so that the cogs of this rotating gear 15 are intertwined with the cogs 16 of the pill carriage 5. A motor 14 is positioned inside the container 2 and connected to the rotating gear 15. The motor 14 is powered upon receiving an electronic signal such that the rotating gear 15 is turned. Because the cogs of the rotating gear 15 are intertwined with the cogs 16 of the pill carriage 5, as the rotating gear 15 rotates, the pill carriage 5 also rotates. It may be seen that the motor 14 is powered such that the pill carriage 5 rotates only so much that the next available pill well 9 is positioned at the opening 6 and therefore exposed to the user for removing the appropriate medication from the newly exposed pill well 9. In this regard, a positioning system 7 that includes a locking component 11 may be implemented to mechanically prevent the pill carriage 5 from rotating any further than necessary to access the appropriate pill well 9, and only when the system 1 recognizes that it is appropriate to move to a new pill well 9 will the locking component 11 release to allow rotation of the pill carriage 5. (In one embodiment, this locking function may be configured to be overridden such that in the event of malfunction or other emergency, any pill well 9 can be accessed if required, as to prevent the locking feature 11 from inadvertently causing a missed dose). Furthermore, it may be seen that additional gear(s) 13 may be utilized in order to cause rotation of the rotating gear 15 and pill carriage 5, by, for example, a worm drive system 8. The double gearing of the motorized worm drive system is shown, for example, in FIGS. 8A-8C. In this case, a worm gear 13 is utilized to change the rotational movement by 90 degrees, and therefore the plane of movement, such that as the worm gear 13 is rotated by the motor 14, the rotating gear 15 rotates, causing the pill carriage 5 to rotate.

In one embodiment, sensors are positioned on or inside the pill container 2 as to detect characteristics associated with the pill container 2. For example, an accelerometer, a gyro sensor, or some combination may be provided to detect movement of the pill container 2. If user interaction with the pill container is detected by these sensors, an alert or notification may be transmitted to the user devices 60, 70 of one or more users 50 associated with the pill container 2 (as described more below).

The system 1 of the present invention includes one or more user devices 60, 70 that are communicatively connected to the pill container 2 via the Internet, Bluetooth, or some other connective means. A user device 60 may be, for example, a smart phone with Bluetooth or WIFI capabilities, allowing the smart phone 60 to communicatively connect to the pill container 2 from close proximity or remote locations. Alternatively, a user device 70 may be, for example, a computer with Bluetooth or internet capabilities. Any other similar devices (such as a tablet, laptop computer, smart watch, etc.) may also be used so long as the user device 60, 70 has the ability to communicatively connect to the pill container 2. As noted above, the system 1 of the present invention has the ability to connect the pill container 2 to a single user device 60, 70 (operated by a single user 50) or by multiple different user devices 60, 70 (which may be operable by multiple different users 50). In any event, it is preferred that where one of the users 50 is a patient-user that at least one of the user devices 60, 70 connected to the pill container 2 is associated with the patient-user of the pill container 2. However, it is understood that in some cases, the patient may not have access to a user device 60, 70, and in such cases, the system 1 can still be used to communicatively connect the pill container 2 to user devices 60, 70 associated with caregivers of the patient or other authorized users 50.

Figure 19:
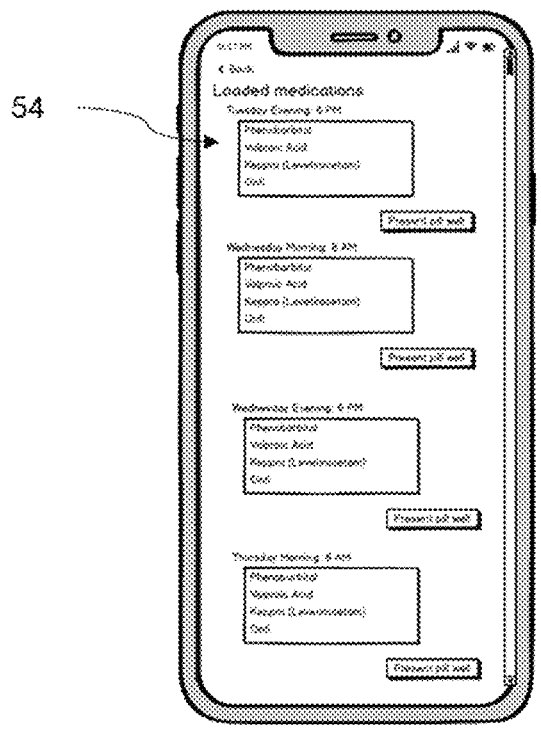
FIG. 19 shows one embodiment of the user interface of the platform of the present invention, particularly showing a breakdown of medications loaded into the pill container associated with the user account on the platform.
Figure 20:
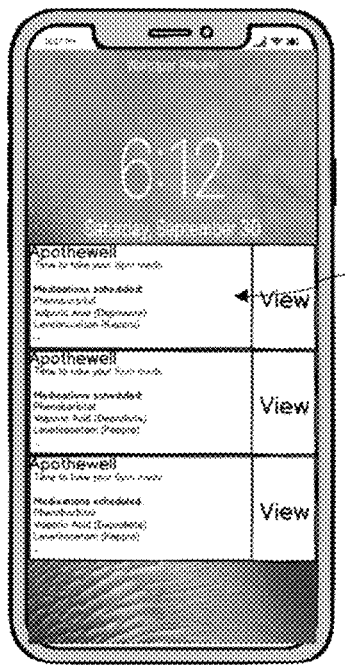
FIG. 20 shows one embodiment of the notification system of the present invention.

As noted previously, in one embodiment, the patient may be the only user 50. In such case, the pill container 2 may be connected to only that patient-user's smart phone 60 (or other user device 70) so that the platform 40 (discussed below) is accessible by that patient-user for monitoring and tracking of the patient-user's own compliance with the prescribed regimen. The patient-user may receive notifications at the smart phone 60 when a refill is necessary, when a dose is skipped, etc., as to allow the patient-user to self-monitor and self-maintain the prescribed regimen, as shown in FIGS. 19 and 20. While it is preferable that the patient have a user device 60, 70 communicatively connected to the pill container 2, as noted above, in some circumstances even a single user device 60, 70 in connection with the pill container 2 may not be that of the patient-user. That is, an embodiment is contemplated where there is a single user or multiple users 50 but the patient himself is not a user 50. Instead, a user device 60, 70 associated with a caregiver may be the only connected device. This may be particularly true where the patient is a minor and the caregiver parent tracks the minor's compliance with the prescribed regimen via the parent's smartphone 60 or computer 70.

While the system 1 can be operable to connect a single user device 60, 70 to a pill container 2, the system 1 is particularly effective when a pill container 2 is connected to multiple different user devices 60, 70. In one embodiment, for example, the pill container 2 may be connected to multiple user devices 60, 70 associated with a single user 50. For example, in the situation where the system 1 is used by a single adult user 60 (who is also the patient) who merely needs better organization for tracking their own compliance with a prescribed medical regimen, the pill container 2 may connect to both the patient-user's smart phone 60 and the same patient-user's computer 70. In this case, the patient-user 50 can access the platform 40 of the present invention from either user device 60, 70, allowing the patient-user 50 to have access, for example, on-the-go or while in the office as the patient-user 50 sees fit. In any event, the system 1 has the ability to notify the user 50 of certain alerts (such as a refill requirement) at both the user's smart phone 60 (as shown for example in FIGS. 19 and 20) and the user's computer 70 so that the user can receive the notification regardless of which user device 60, 70 is more readily available.

In an alternative embodiment, for example, the pill container 2 may be communicatively connected to multiple user devices 60, 70 associated with and operable by multiple different users 50. This embodiment may be particularly suitable, for example, in scenarios where a dependent (such as a minor child) is prescribed a particular medical regimen and the dependent's caregivers (such as parents) desire to be kept informed of the dependent's compliance with the medical regimen. In such a case, the dependent (the patient user) may connect to the pill container 2 through their own user device (such as a smart phone 60), and each of the caregivers may also connect to the pill container 2 through their own user devise (such as their own smart phones 60 or computers 70). In this case, alerts and data from the pill container 2 may be transmitted to each of the different users 50 so that both the dependent and caregivers known when a dose is missed, when a prescription needs to be refilled, or when some other important notification arises. This may be particularly useful in situations where it is desirable to give the dependent patient user more independence, as they are able to track and monitor their own compliance with the prescribed regimen, but a caregiver or multiple caregivers can simultaneously track and monitor compliance and interfere as necessary. For example, in assisted living situations, a nurse or aide may have the ability to monitor the compliance or non-compliance of one or more patient residents from his or her computer or other user device.

The system of the present invention includes a computerized platform 40 that allows users 50 to access information associated with and corresponding to the operation and use of the pill container 2. The platform 40 is accessible by one or more users 50 via user devices 60, 70, as described above. The platform 40 is operable to receive input information from the users 50, and based on use of the pill container 2, notify select users of various information associated with the particular pill container 2. Of course, because it is contemplated that a great number of pill containers 2 (each associated with different patient's and different medical regimens) will be in use by different users at any given time, user devices 60, 70 need to be associated with a particular pill container 2 so that users 50 only receive information associated with the use of that pill container 2 (and not information associated with the use of a pill container for some other patient with whom the user is not connected). It should be noted, of course, that caregivers can be associated with multiple patients and therefore multiple pill containers 2. It is also contemplated that a patient could act as the caregiver for another patient such that the first patient is associated with both their own pill container and the pill container of the other patient.

In the preferred embodiment, registration of a pill container 2 and association of the pill container 2 with a particular user device 60 is facilitated by pairing the user device 60 with the pill container 2 via Bluetooth or some other short frequency communications means. This will allow each user (whether a patient-user or non-patient-user) to selectively pair his or her user device(s) 60 only with the pill container 2 of interest. If a user does not have the ability to connect via Bluetooth or other similar means, the pill container 2 can be registered and connected to a user's device 60 via a unique code displayed on the pill container 2 and entered into the platform 40. Once a user device 60 is communicatively connected to the pill container 2, the pill container 2 can transmit information collected to the user device 60 by various means, as discussed below. In one embodiment, where there are multiple users 50 associated with a single pill container 2, one of such users (such as the primary caregiver, for example) may be provided with administrator rights, allowing that user to control access rights of all other users for the pill container 2. This may allow the administrator to allow, for example, all users to receive notifications (such as for a missed dose) but allow the administrator to prohibit all other users from modifying the medication list or dosing schedule. Furthermore, the pill container 2 and device of the present invention may be useful for insurance companies, hospitals, clinics, pharmacies, or other similar entities 20 to both track and understand their customers' (e.g. patients') adherence to medical regimen as well as provide a channel for these entities to directly communicate and educate their customers. In this regard, these entities may be given certain caregiver access to the platform 40 and data associated with particular patients and their pill containers 2. As noted above, restrictions may be placed on these accounts so that they only have the ability to access information necessary or allowed by the users.

Figure 11:
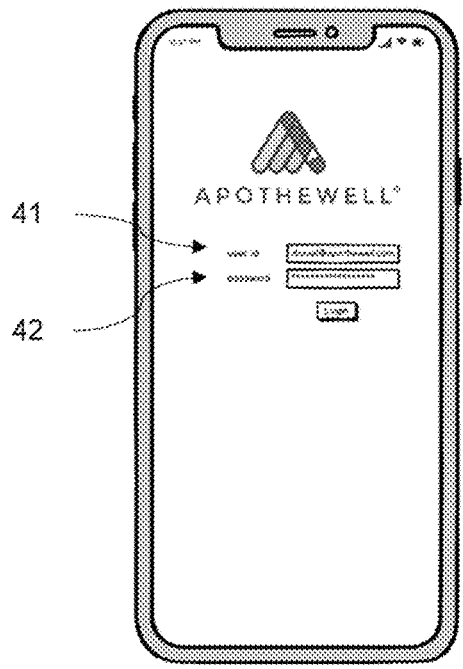
FIG. 11 shows one embodiment of the login interface of the platform of the present invention.
Figure 12:
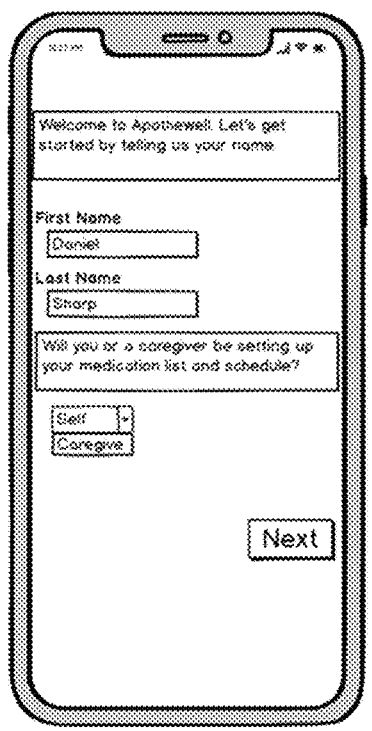
FIG. 12 shows one embodiment of the user interface of the platform of the present invention, particularly showing input fields for patient and/or user information.
Figure 13:
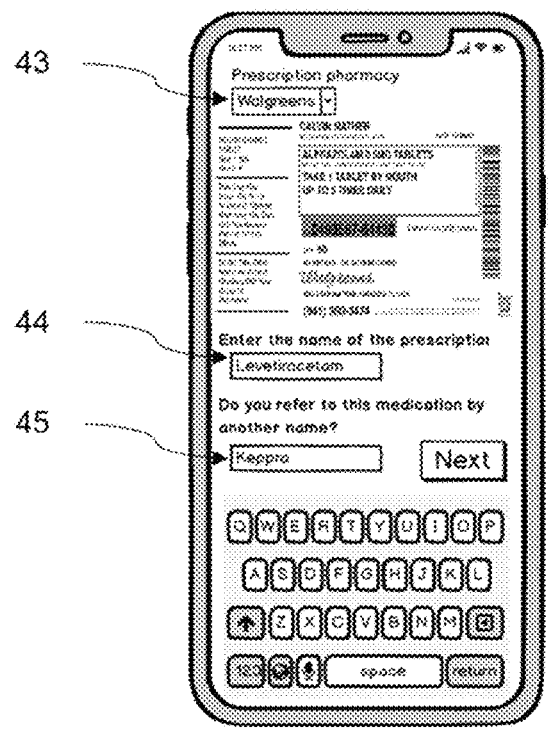
FIG. 13 shows one embodiment of the user interface of the platform of the present invention, particularly showing input fields for prescription identification information.
Figure 14:
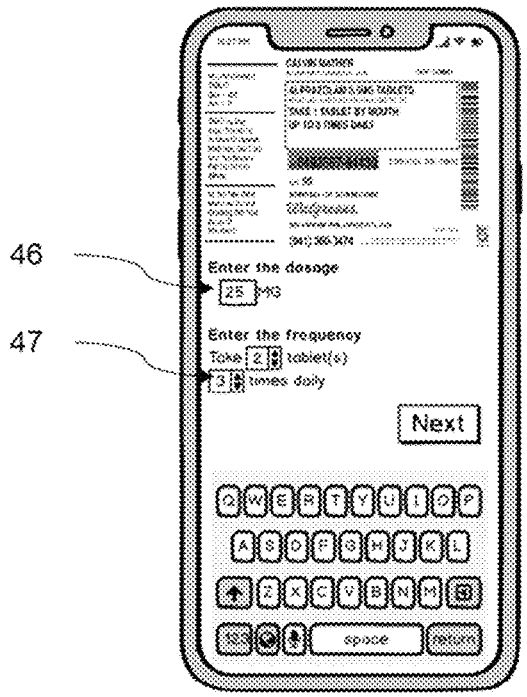
FIG. 14 shows one embodiment of the user interface of the platform of the present invention, particularly showing input fields for prescription dosage and frequency information.

In order for the pill container 2 to be useful for monitoring compliance with a prescribed medical regimen, the pill container 2 and platform 40 must be given sufficient information about the medical regimen to know if compliance is achieved. A user interface of the platform (as shown for example in FIGS. 9-20) is utilized to input certain information about the patient, medical regimen, etc. that helps monitor compliance through use of the pill container 2. Of course, given the sensitive nature of the information provided to and associated with the use of the pill container 2, the platform 40 preferably requires identification authentication before providing a user access to such information. In the preferred embodiment, as shown in FIG. 11, a username 41 and password 42 are required to better secure the sensitive information, and prior to or upon initial use of the pill container 2, such username 41 and password 42 must be created. It is preferred that for every subsequent attempt to use the platform 40 to access or change information related to the associated pill container 2 or medical regimen that the username 41 and password 42 is be required before the user has access to the user interface 40 and associated information. It is contemplated, of course, that the authentication can be via other means such as fingerprint recognition, facial recognition, or other biometric means, or via passcodes, PINs, or other authentication means. Upon an initial access to the platform 40, the user may be required to input certain information about the pill container 2 and prescribed medical regimen. For example, as shown in FIG. 12, the user may input his or her name, the patient's name if the patient is different from the user, and a determination whether the patient or a caregiver is primarily responsible for setting and monitoring the prescribed medical regimen. Additional information that may be required includes information related to the prescribed medications, including the pharmacy 43 that fulfilled the prescription, the name of the medication (including generic names 44 and brand names 45), the dosage amount 46 for the medication, and the dosage frequency 47 for the medication, as shown for example in FIGS. 13-14. Information related to the ability to seek refills for the medication (including the amount available) may also be provided, as well as information related to the number of pills in the bottle at the time this information is collected (in one embodiment, it may be seen that the pill container 2 is first used with a brand new bottle of medication, but it is also possible that the pill container 2 is first used at some point in the middle of a prescribed bottle, and thus the number of remaining pills will need to be determined). In one embodiment, the platform 40 is pre-loaded with various label layouts of popular pharmacies such that the user interface for inputting prescription medication mimics the label of the pharmacy selected by the user. This reduces the mental effort of interpreting medication dosage labels. In yet another embodiment, the user device 60 may be used to snap a photograph or scan of the medication's label and the platform 40 may auto-populate information based on the photograph or scan provided.

Figure 15:
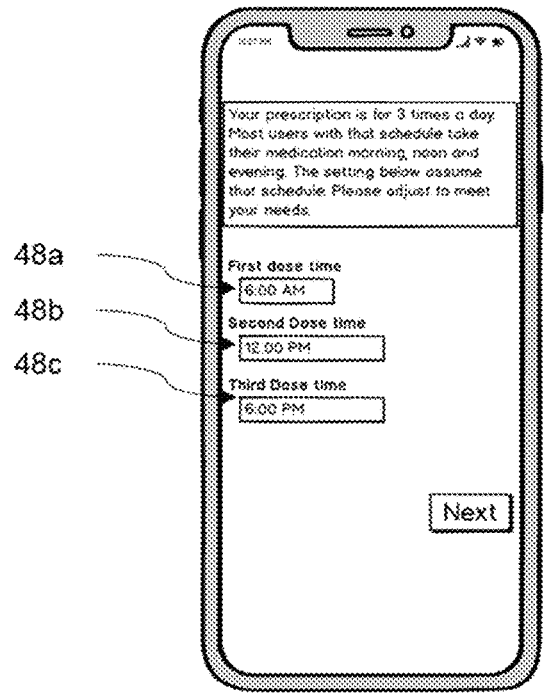
FIG. 15 shows one embodiment of the user interface of the platform of the present invention, particularly showing a suggested dosing schedule.

Once the information about a new medication is provided via the user interface, the platform 40 allows the user to set a dosage schedule. For example, as shown in FIG. 15, where the platform 40 learns that a particular medication is supposed to be taken three times per day, the user is asked to select a first dose time 48a, a second dose time 48b, and a third dose time 48c. In one embodiment, the platform 40 may suggest to the user the appropriate dose times 48a, 48b, 48c, allowing the user to adjust the scheduled times as needed. In the event the user attempts to set dose times that are too close together, the platform 40 may prohibit such modification of the dosing schedule. Of course, in the event that multiple medications are prescribed, information related to each medication will need to be input separately as to ensure accuracy. In the event multiple medications are required throughout the day, the platform 40 will attempt to align dose times such that multiple medications can be taken on the same dosing schedule.

Figure 16:
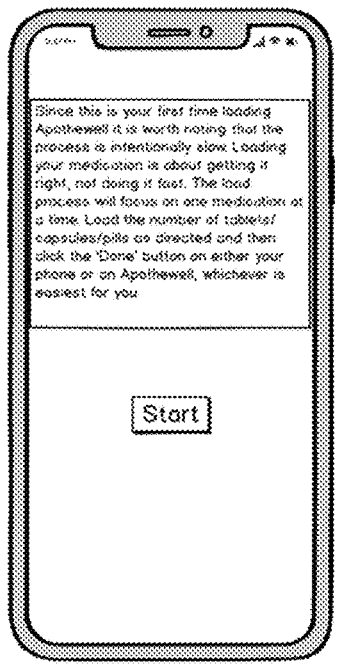
FIG. 16 shows one embodiment of the user interface of the platform of the present invention, particularly showing the beginning of the pill carriage load guidance.
Figure 17:
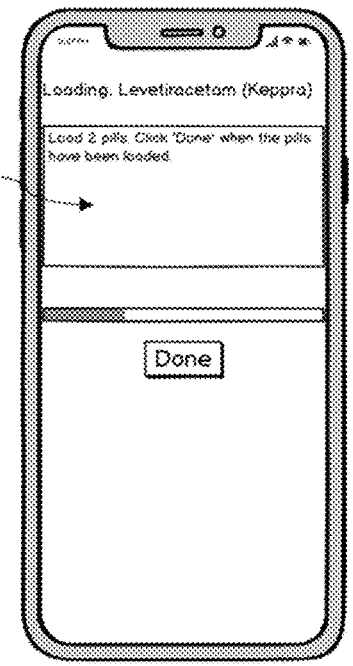
FIG. 17 shows one embodiment of the user interface of the platform of the present invention, particularly showing the pill carriage load guidance process.
Figure 18:
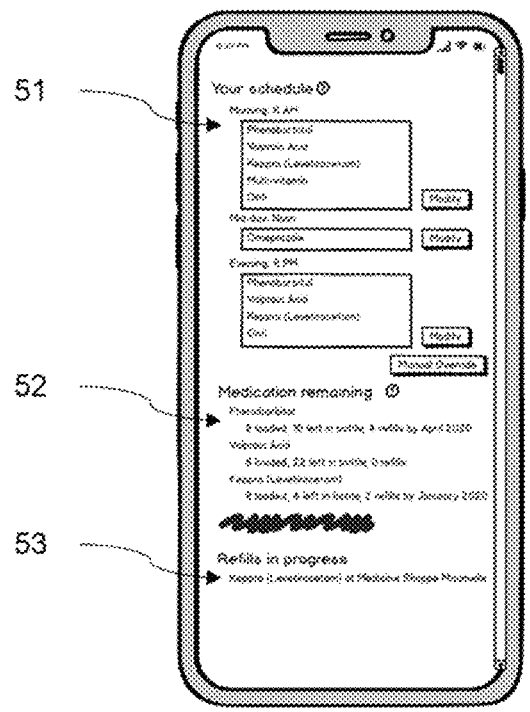
FIG. 18 shows one embodiment of the user interface of the platform of the present invention, particularly showing the medication schedule corresponding with the pill container associated with the user account on the platform.

After the information is collected for all prescribed medications and a dosing schedule for each medication has been set, the platform 40 will walk the user through loading each medication into the pill container 2 according to the patient's overall dosing schedule, as shown for example in FIGS. 15-16. For example, the platform 40 may instruct the user to load two pills for Medication A into each of the pill wells 9, because Medication A is taken at each dosing time in the dosing schedule. Next, the platform 40 may instruct the user to load one pill for Medication B into each pill well 9, because Medication B is taken at each dosing time in the dosing schedule, but the dose only requires one pill for Medication B instead of the two required for Medication A. Then, the platform 40 may instruct the user to load one pill for Medication C into every other pill well 9, because Medication C does not need to be taken at every dosing time (for example, Medication C may only be needed twice per day, while Medications A and B are needed three times per day). The platform 40 will instruct the user to load each of the input medications according to the determined dosing schedule. Based on a known number of pill wells 9 in the pill container 2 and based on the information provided by the user identifying the number of pills for each medication at input, the pill container 2 and system 1 can automatically determine for each medication (a) the number of pills loaded into each pill well 9, (b) the total number of pills loaded into all pill wells 9 combined, and (c) the number of pills remaining in the bottle. Based off of this information, the platform 40 can determine the appropriate date for seeking refill of the prescribed medication. Likewise, because the pill container 2 has a known number of pill wells 9, the user can identify the dosing time associated with the first pill well 9 (for example Tuesday evening at 6 pm), and based off of the dosing schedule identified, the platform 40 can identify the dosing time associated with each of the remaining pill wells 9 (for example, the second pill well may be associated with Wednesday morning at 8 am, the third with Wednesday evening at 6 pm, etc.). Based off of this information, the platform 40 can provide the user(s) with directions for maintaining compliance with the regimen by indicating when it is appropriate to take the dose of medication contained in each of the pill wells 9. In one embodiment, the platform 40 may provide the user(s) with a schedule of doses 55 or may even place event reminders on a calendar associated with the user device 60, as shown in FIG. 20.

Figure 21:
FIG. 21 shows one embodiment of the notification system of the present invention.
Figure 22:
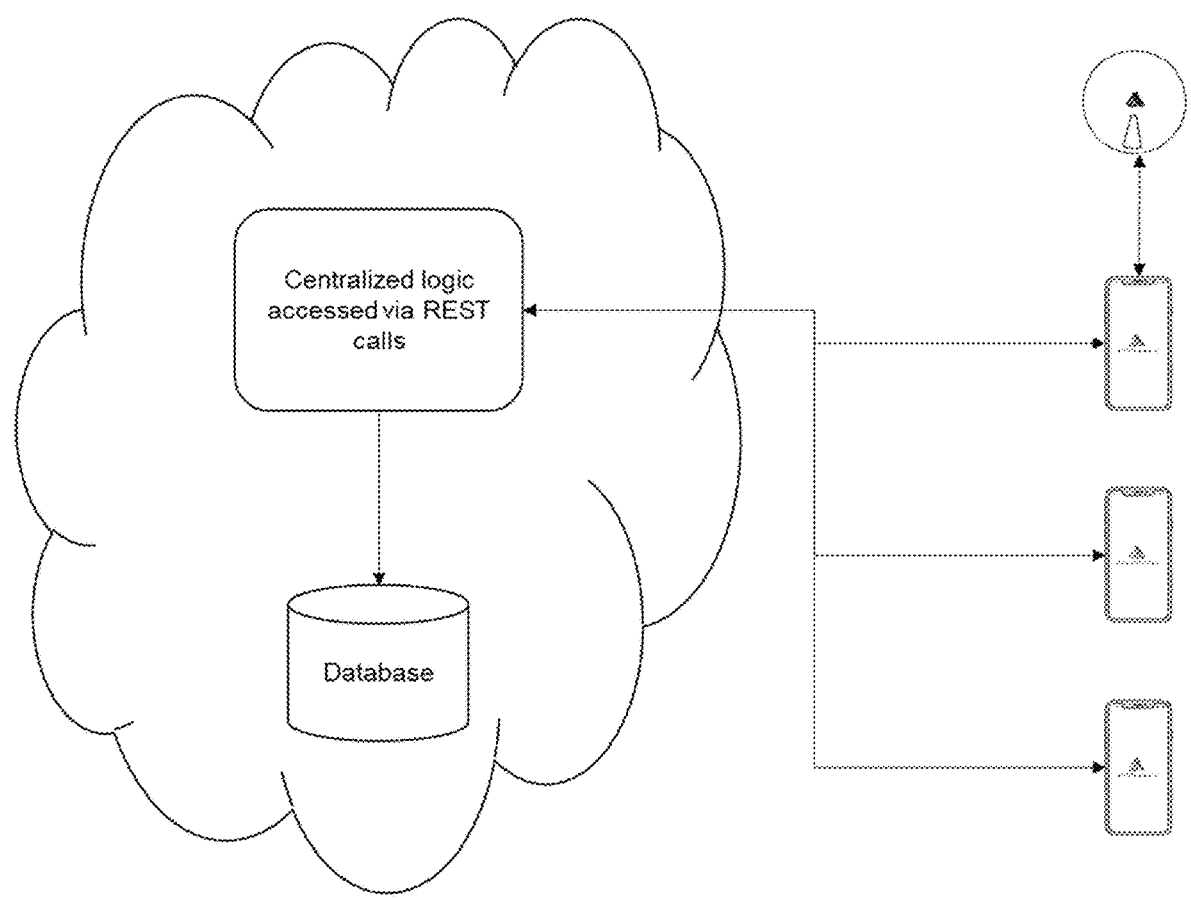
FIG. 22 shows a diagram depicting one embodiment of the centralized control mechanism of the present invention.

As noted above, the pill container 2 for a particular medical regimen is connected to one or more user devices 60. While the platform 40 is configured to initially set and provide the user with a dosing schedule, the platform 40 is also configured to continuously monitor compliance with the set schedule. In connection with the monitoring of compliance, the platform 40 is configured to send alerts or notifications 56 to the user device(s) 60 associated with the pill container 2, the alerts and notifications associated with various events, as shown for example in FIG. 21. It is understood that the alerts or notifications 56 may be repeated, perhaps in increasing frequency, if compliance is not achieved. For example, as noted above, the pill container 2 may include sensors that record movement or interaction with the pill container 2. If movement is detected at a time that does not correspond to a scheduled dosing time, the platform 40 may alert all (or only some) user devices 60, 70 associated with the pill container 2 that an attempt to mis-dose has been detected. In addition, the platform 40 may notify the user(s) of the appropriate dosage time. In one embodiment, the pill container 2 may even prevent dosage at a time outside of the set schedule—by, for example, preventing the lid of the container 2 to be opened to access the pill well 9, or, for example, by preventing rotation of the pill carriage 5 to a new pill well 9. Other events that may warrant alerts or notifications 56 to user devices 60 include alerts that a prescription refill is needed or alerts that a dose has been missed (for example, if the pill container 2 does not detect movement within a certain time window around a set dosing schedule). In the event the user 50 identifies through the platform 40 that a new medication has been started or an existing medication has been ended, an alert or notification may be provided to instruct the user 50 to load new medications (or remove discontinued medications) from pill wells 9 as needed. It is contemplated that the pill container 2 may communicate with the platform 40 directly through a cell network or wireless internet to transmit information to and receive information from the platform 40. In the preferred embodiment, however, the user devices 60, 70 communicate to the backend API services 30 (which are responsible, for example, for authenticating users, securing storing user data, and securing disseminating information to users as needed). and pass information to the pill container 2 via the Bluetooth connection.

In one embodiment, the pill container 2 may include a camera (or multiple cameras) inside the internal compartment in order to scan and record the pills contained in each of the pill wells 9. Machine learning may be implemented to identify misloaded pill wells 9 by, for example identifying specific pills that are in the pill well 9 that should not be in the pill well 9, or determining a total number of pills in the given pill well 9 is different than the number of pills that should be in that pill well 9. In one embodiment, the pill container 2 may allow users to reserve certain pill wells 9 to contain "as needed" medication. These medications are those that are prescribed on an as needed basis, but do not require daily dosing. For example, some "as needed" medications may be emergency dose that should only be administered as a last option. It is contemplated, then, that the pill wells 9 for these "as needed" medications may not be included in the daily rotation of pill wells 9 (and thus the rotation of the pill carriage 5 may automatically skip these pill wells 9 during normal operation of the dosing schedule). Because the pill wells 9 are loaded with guidance from the platform 40, which is based off information input by the user 50, the platform 40 knows which pill wells 9 contain the "as needed" medication. Thus, the pill container 2 has the ability to skip these pill wells 9 as the pill carriage 5 rotates new pill wells 9 to the opening 6 position. It's contemplated that the platform 40 may give users 50 (or only certain uses, such as the primary caretaker) the ability to rotate the pill carriage 5 to the "as needed" pill well 9 allowing the user access to that "as needed" medication. This release could be facilitated by a remote user, such that a caregiver, for example, could provide a patient access to the "as needed" medications even when the caregiver is not physically near the patient or pill container 2.

In one embodiment, the pill container 2 and platform 40 are useful for allowing administration of medicines even in cases of partial dose availability. That is, there may be a situation where the user is loading the pill container 2 but there is only enough of a certain medication to partially load that medication into the pill wells 9, even if other medications are plentiful to be loaded into all pill wells 9. Because the system 1 is knowledgeable about the medication loaded into each different pill well 9, the system 1 can track which pill wells 9 have complete doses (and which are missing one or more medications). This allows for continued use of the system 1 until more medication is required without having to unload partial pill wells 9.

Furthermore, it may be seen that in order to maximize the efficiency of the smart pill container system, centralization of the logic associated with the smart pill container system may be valuable. Many electronic pill cases, i.e. pill cases that have on-board hardware and software to add user functionality, decentralize the logic and control of the pill cases so that each pill case is an independent entity. The pill case might communicate and send data such as adherence metrics or caregiver notifications of missed dosages to a centralized location but the majority of the logic originates from the pill case. By tightly coupling a pill case with a smart device and then also centralizing the logic, i.e. moving the origin of control from the pill case to a server environment, a much-improved user experience is possible. By having the smart device work in conjunction with the pill case, alerts can be sent until the user interacts with the pill case. By moving the core logic from the pill case to a centralized location, features like allowing multiple users to edit medication list or change medication schedules become trivial. It also becomes trivial to create specialized software to manage a specific morbidity. An example would be HIV or cancer treatments. A custom solution for cancer treatments could be very aggressive with schedule alerting, alerting multiple people every few minutes until the pill case is interacted with. A custom solution for HIV treatment could instead focus on tracking on hand pill amounts to make sure refills are submitted in a timely manner and providing load guidance to ensure the pill case is always loaded correctly. Since a solution for each niche can be developed and distributed via a centralized system, custom solutions for each niche becomes a financially viable option.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. In particular, the terms "comprise" and "comprising" should be interpreted as referring to elements, components, or steps in a non-exclusive manner, indicating that the referenced elements, components, or steps may be present, or utilized, or combined with other elements, components, or steps that are not expressly referenced. When a Markush group or other grouping is used herein, all individual members of the group and all combinations and subcombinations possible of the group are intended to be individually included. All references cited herein are hereby incorporated by reference to the extent that there is no inconsistency with the disclosure of this specification. When a range is stated herein, the range is intended to include all sub-ranges within the range, as well as all individual points within the range. When "about," "approximately," or like terms are used herein, they are intended to include amounts, measurements, or the like that do not depart significantly from the expressly stated amount, measurement, or the like, such that the stated purpose of the apparatus or process is not lost.

The present invention has been described with reference to certain preferred and alternative embodiments that are intended to be exemplary only and not limiting to the full scope of the present invention, as set forth in the appended claims.

The invention claimed is:

1. A smart pill container system comprising:
   a. a smart pill container operable to store and administer a patient's medication according to a prescription associated with the patient;
   b. a computerized platform operable to digitally translate natural language prescription information to a structure and form useful for operating the smart pill container, wherein the computerized platform is operable to:
      i. abstract a frequency data value associated with the prescription, wherein abstracting the frequency data value comprises:
         1. Providing a series of at least two time slots;
         2. Based on the frequency data value associated with the prescription, assigning at least one of the time slots as an active time slot, wherein each active time slot is associated with a dosing time;
         3. If based on the frequency data value associated with the prescription there is assigned more than one active time slot, determining a number of instances where all active time slots are equally distributed throughout the series of time slots;
         4. Recording each instance where all active time slots are equally distributed through the series of time slots as an abstracted frequency value;
         5. And storing each abstracted frequency value in a database associated with the smart pill container system;
      ii. abstract a temporal data value associated with the prescription, wherein abstracting the temporal data value comprises assigning an as of date value to each of the abstracted frequency values, thereby creating a number of date-value pairs;
      iii. based on the date-value pairs, build a dosing schedule for use with the smart pill container; and
      iv. provide a user instructions for loading medication into the smart pill container based on the determined dosing schedule.

2. The smart pill container system of claim 1, further comprising a centralized server, wherein the smart pill container is in communication with the computerized platform via the centralized server.

3. The smart pill container system of claim 2, further wherein the data-value pairs are stored at a database at the centralized server.

4. The smart pill container system of claim 1, further wherein the smart pill container comprises:
   a. a housing forming an internal compartment;
   b. a rotatable pill carriage positioned inside the internal compartment, the pill carriage comprising a number of pill wells configured to store one or more medications; and
   c. an opening in the housing;
   wherein the opening is positioned to provide user access to the one or more pills stored in the number of pill wells in series according to the determined dosing schedule.

5. The smart pill container system of claim 1, further comprising a drive system configured to cause rotation of the pill carriage.

6. The smart pill container system of claim 1, further comprising a locking mechanism configured to prevent rotation of the pill carriage between the first dosing time and the second dosing time.

7. The smart pill container system of claim 1, further comprising at least one user device in communication with the smart pill container and configured to accessed the computerized platform.

8. The smart pill container system of claim 7, wherein the computerized platform is further configured to monitor whether the user accesses the medications stored in the smart pill container to determine user compliant with the dosing schedule.

9. The system of claim 7, wherein the user device is associated with at least one of an insurance provider of the patient, a pharmacy provider of the patient, and a health care provider of the patient.

10. The system of claim 7, wherein the user device is a smartphone.

11. The system of claim 7, wherein the user device is associated with the patient.

12. The system of claim 7, wherein the user device is associated with a caregiver of the patient.

* * * * *